US006436053B1

(12) United States Patent
Knapp, II et al.

(10) Patent No.: US 6,436,053 B1
(45) Date of Patent: Aug. 20, 2002

(54) METHOD AND APPARATUS FOR ENHANCING PATIENT COMPLIANCE DURING INSPIRATION MEASUREMENTS

(75) Inventors: Keith N. Knapp, II, Townsend; Alan M. Cohen, Newton, both of MA (US)

(73) Assignee: Boston Medical Technologies, Inc., Wakefield, MA (US)

( * ) Notice: Subject to any disclaimer, the term of this patent is extended or adjusted under 35 U.S.C. 154(b) by 0 days.

(21) Appl. No.: 09/507,770

(22) Filed: Feb. 18, 2000

Related U.S. Application Data

(63) Continuation-in-part of application No. 08/942,710, filed on Oct. 1, 1997, now Pat. No. 6,106,481.
(60) Provisional application No. 60/153,902, filed on Sep. 14, 1999.

(51) Int. Cl.[7] ................................................. A61B 5/08
(52) U.S. Cl. ........................................ 600/538; 600/529
(58) Field of Search ................................. 600/529, 532, 600/533, 534, 535, 537, 538, 539

(56) References Cited

U.S. PATENT DOCUMENTS

| | | |
|---|---|---|
| 2,649,573 A | 8/1953 | Goldberg et al. |
| 3,142,796 A | 7/1964 | Goldberg et al. |
| 3,340,867 A | 9/1967 | Kubicek et al. |
| 3,407,818 A | 10/1968 | Costanzo |
| 3,560,845 A | 2/1971 | Goldberg et al. |
| 3,731,184 A | 5/1973 | Goldberg et al. |
| 3,925,762 A | 12/1975 | Heitlinger et al. |
| 3,991,304 A | 11/1976 | Hillsman |
| 4,023,563 A | 5/1977 | Reynolds et al. |
| 4,031,885 A | 6/1977 | Davis et al. |
| 4,036,215 A | 7/1977 | Doll |
| 4,137,910 A | 2/1979 | Murphy |
| 4,216,779 A | 8/1980 | Squires et al. |
| 4,240,442 A | 12/1980 | Andresen et al. |
| 4,308,872 A | 1/1982 | Watson et al. |
| 4,346,718 A | 8/1982 | Morris |
| 4,364,397 A | 12/1982 | Citron et al. |
| 4,367,753 A | 1/1983 | Jirak |
| 4,408,614 A | 10/1983 | Weaver et al. |
| 4,433,693 A | 2/1984 | Hochstein |
| 4,440,177 A | 4/1984 | Anderson et al. |
| 4,446,872 A | 5/1984 | Marsoner et al. |
| 4,506,678 A | 3/1985 | Russell et al. |
| 4,513,295 A | 4/1985 | Jones et al. |
| 4,559,947 A | 12/1985 | Renger et al. |
| 4,649,929 A | 3/1987 | Weaver et al. |
| 4,679,144 A | 7/1987 | Cox et al. |
| 4,692,148 A | 9/1987 | Kantrowitz et al. |
| 4,721,114 A | 1/1988 | DuFault et al. |
| 4,777,960 A | 10/1988 | Berger et al. |
| 4,807,640 A | 2/1989 | Watson et al. |
| 4,815,473 A | 3/1989 | Watson et al. |
| 4,819,654 A | 4/1989 | Weaver et al. |
| 4,832,038 A | 5/1989 | Arai et al. |
| 4,862,361 A | 8/1989 | Gordon et al. |

(List continued on next page.)

FOREIGN PATENT DOCUMENTS

| | | | |
|---|---|---|---|
| EP | 0 856 334 | 8/1998 | |
| GB | 2113101 | 3/1983 | .......... A61M/16/00 |
| WO | WO 94 14374 | 7/1994 | |
| WO | WO 97/12546 | 10/1997 | |
| WO | WO 99 16506 | 4/1999 | |

*Primary Examiner*—Kevin Shaver
*Assistant Examiner*—Navin Natnithithadha
(74) *Attorney, Agent, or Firm*—Daly, Crowley & Mofford, LLP

(57) ABSTRACT

A system for enhancing patient compliance with a predetermined breathing pattern during inspiration measurements utilizes patient feedback based on inspiration flow. The measured inspiration flow is displayed on a first display and a target inspiration flow is display on a second display, preferably, disposed adjacent to the first display to facilitate visual comparison. The patient is instructed to breathe in manner that causes the measured inspiration flow display to match, or flow the target inspiration flow display.

14 Claims, 14 Drawing Sheets

U.S. PATENT DOCUMENTS

| | | |
|---|---|---|
| 4,869,262 A | 9/1989 | Orr et al. |
| 4,870,974 A | 10/1989 | Wang |
| 4,889,131 A | 12/1989 | Salem et al. |
| 4,905,708 A | 3/1990 | Davies |
| 4,909,260 A | 3/1990 | Salem et al. |
| 4,913,146 A | 4/1990 | DeCote, Jr. |
| 4,930,517 A | 6/1990 | Cohen et al. |
| 4,934,377 A | 6/1990 | Bova et al. |
| 4,947,857 A | 8/1990 | Albert et al. |
| 4,979,110 A | 12/1990 | Albrecht et al. |
| 4,984,158 A | 1/1991 | Hillsman |
| 5,025,794 A | 6/1991 | Albert et al. |
| 5,027,824 A | 7/1991 | Dougherty et al. |
| 5,148,812 A | 9/1992 | Verrier et al. |
| 5,156,148 A | 10/1992 | Cohen |
| 5,159,935 A | 11/1992 | Sackner et al. |
| 5,167,506 A | 12/1992 | Kilis et al. |
| 5,269,301 A | 12/1993 | Cohen |
| 5,277,189 A | 1/1994 | Jacobs |
| 5,285,793 A | 2/1994 | Slokvut et al. |
| 5,299,119 A | 3/1994 | Kraf et al. |
| 5,301,678 A | 4/1994 | Watson et al. |
| 5,312,441 A | 5/1994 | Mader et al. |
| 5,316,008 A | 5/1994 | Suga et al. |
| 5,330,508 A | 7/1994 | Gunderson |
| 5,333,106 A | 7/1994 | Lanpher et al. |
| 5,360,008 A | 11/1994 | Campbell, Jr. |
| 5,390,679 A | 2/1995 | Martin |
| 5,394,873 A | 3/1995 | Kraemer et al. |
| 5,400,795 A | 3/1995 | Murphy et al. |
| 5,423,325 A | 6/1995 | Burton |
| 5,437,285 A | 8/1995 | Verrier et al. |
| 5,450,850 A | 9/1995 | Iinuma |
| 5,483,969 A | 1/1996 | Testerman et al. |
| 5,485,847 A | 1/1996 | Baker, Jr. |
| 5,497,778 A | 3/1996 | Hon |
| 5,509,404 A | 4/1996 | Lloyd et al. |
| 5,520,190 A | 5/1996 | Benedict et al. |
| 5,543,012 A | 8/1996 | Watson et al. |
| 5,546,952 A | 8/1996 | Erickson |
| 5,582,182 A | 12/1996 | Hillsman |
| 5,627,327 A | 5/1997 | Zanakis |
| 5,724,580 A | 3/1998 | Levin et al. |

METHOD AND APPARATUS FOR ENHANCING PATIENT COMPLIANCE DURING INSPIRATION MEASUREMENTS

CROSS-REFERENCE TO RELATED APPLICATIONS

This application is a continuation-in-part application of U.S. patent application Ser. No. 08/942,710, filed Oct. 1, 1997 now U.S. Pat. No. 6,106,481 and entitled METHOD AND APPARATUS FOR ENHANCING PATIENT COMPLIANCE DURING INSPIRATION MEASUREMENTS and claims priority under 35 U.S.C. §119(e) to U.S. Provisional patent application Ser. No. 60/153,902, filed on Sep. 14, 1999 and entitled METHOD AND APPARATUS FOR ENHANCING PATIENT COMPLIANCE DURING INSPIRATION MEASUREMENTS, both of which are incorporated herein by reference in their entirety.

STATEMENTS REGARDING FEDERALLY SPONSORED RESEARCH

Not applicable.

BACKGROUND OF THE INVENTION

Various medical diagnostic apparatus require that aspects of a patient's respiration, such as inspiration volume, be measured. Illustrative of such apparatus are heart rate variability assessment monitors which can be used in the diagnosis and treatment of various disease states.

In certain applications, it is advantageous to have the patient breathe in a particular manner when measuring inspiration volume. As one example, in neuropathy diagnosis, it is desirable that the patient breathe at a predetermined, constant frequency, such as on the order of six breaths/minute, or 0.10 Hz. However, even with specific instructions, it is difficult to ensure that the patient will breathe at the constant, predetermined frequency (i.e., to ensure "patient compliance" with a desired breathing pattern). Further, even if the patient complies closely with the desired breathing pattern, a patient's breathing often varies between tests, rendering the results of long-term testing less meaningful due to inter-test variability.

In an effort to enhance patient compliance and thus to reduce inter-test variability, some conventional systems include interactive mechanisms by which the patient is instructed to breathe in accordance with a particular pattern. For example, in a monitor sold under the product name HRView™ versions I and II by Boston Medical Technologies, Inc., different audio tones are used to indicate to the patient when to inhale and when to exhale. While this arrangement improves patient compliance and reduces inter-test variability, an even more effective way of ensuring patient compliance with a particular breathing pattern is desirable.

BRIEF SUMMARY OF THE INVENTION

Apparatus and methods for enhancing a patient's compliance with a predetermined breathing pattern include the use of feedback based on inspiration, or breath flow. Inspiration flow is the rate of breathing over time. A system according to the invention includes a device for measuring the inspiration flow of a patient, a first display on which the patient's measured inspiration flow is displayed and a second display on which a target inspiration flow is displayed. The system further includes a processor for controlling the first display in response to the measured inspiration flow and for controlling the second display in accordance with a predetermined function. The patient is instructed to breathe so as to cause the measured inspiration flow display to match, or follow the target inspiration flow display.

With this arrangement, patient compliance with a predetermined breathing pattern is achieved in a highly accurate and repeatable manner. This is because modifying one's breathing to emulate an inspiration flow pattern has been found to be a relatively easy task, for example as compared to emulating an inspiration volume pattern. Further, inspiration flow feedback does not suffer from certain errors, such as may be associated with converting a measured flow signal into a volume signal. Thus, patient feedback based on inspiration flow results in a precise and repeatable matching of actual inspiration flow to a target inspiration flow.

Preferably, each of the first and second displays comprises a corresponding plurality of display elements disposed adjacent to one another in order to facilitate visual comparison. In one embodiment, the display elements are LEDs arranged in the form of a bar graph.

In one embodiment, the processor controls the second, target display portion according to a predetermined mathematical function. Illustrative mathematical functions include a sine wave function, a square wave function, a triangular function, a trapezoidal function, a chirp function or a combination of two or more such functions.

In accordance with a further aspect of the invention, the processor is responsive to the measured inspiration flow for computing the patient's inspiration volume. In a metronomic deep breathing test, the inspiration volume is used to compute a deep breathing maximum level which is used to prompt the patient to breath to a predetermined percentage of lung capacity. The inspiration volume is further processed to determine the extent to which the patient's breathing pattern matches the target breathing pattern.

Also described is a method for enhancing patient compliance with a predetermined breathing pattern including the steps of measuring the patient's inspiration flow, displaying the measured inspiration flow, displaying a target inspiration flow in accordance with a predetermined function, and instructing the patient to breathe in a manner which causes the measured inspiration flow display to match, or follow the target inspiration flow display.

According to a further aspect of the invention, a system for improving patient compliance with a predetermined breathing pattern includes a display for displaying the measured inspiration flow of the patient. The display includes a maximum flow display portion which indicates when the patient's inhalation flow exceeds a predetermined maximum level and a minimum flow display portion which indicates when the patient's exhalation flow falls below a predetermined minimum level. Both the predetermined maximum level for inhalation flow and the predetermined minimum level for exhalation flow are functions of the measured inspiration flow of the patient. The display further includes a target inspiration flow portion for displaying a target inspiration flow.

With this arrangement, a patient is provided with an indication that their inspiration flow (i.e., breathing rate) is either too high or too low. In this way, the patient is provided with further guidance in controlling his or her breathing so as to cause the measured inspiration flow to match the target inspiration flow, thereby further enhancing the accuracy and inter-test repeatability of the breathing test. This feature is particularly advantageous when conducting metronomic deep breathing testing for heart rate variability analysis in

BRIEF DESCRIPTION OF THE DRAWINGS

The foregoing features of this invention, as well as the invention itself, may be more fully understood from the following description of the drawings in which.

DETAILED DESCRIPTION OF THE INVENTION

Figure 1:
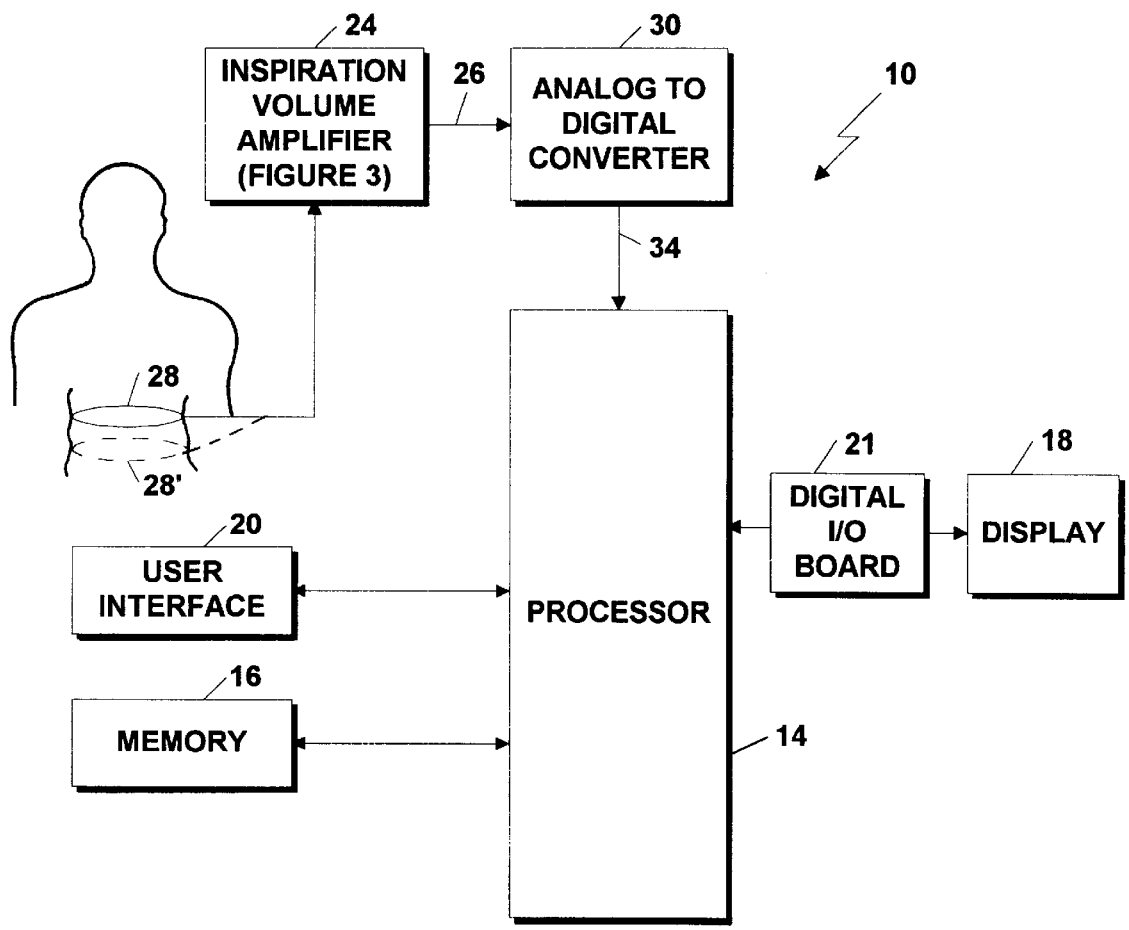
FIG. 1 is a block diagram of a medical diagnostic system including apparatus for measuring inspiration volume and for enhancing patient compliance with a predetermined breathing pattern.

Referring to FIG. 1, a medical diagnostic system 10 includes apparatus and implements techniques for measuring and displaying a patient's inspiration volume. The system 10 may be one of various types of medical diagnostic apparatus in which it is desired to measure a patient's inspiration volume. One illustrative system is a heart rate variability analysis system as described in connection with FIG. 9 below.

The system 10 further includes apparatus and implements techniques for improving patient compliance with performance of a desired task during measurements, such as breathing in a predetermined pattern during inspiration volume measurements. It will be appreciated by those of ordinary skill in the art that the apparatus and techniques described herein are suitable for enhancing patient compliance with performance of a desired task during various types of measurements. However, for simplicity of illustration, the system is described with particular reference to enhancing patient compliance with a predetermined breathing pattern during inspiration volume measurements.

The system 10 includes a processor 14 in electrical communication with a memory 16, a display 18 and a user interface 20. An inspiration volume amplifier circuit 24 is coupled to a patient interface 28 and includes circuitry for measuring the inductance of the patient interface to provide an analog amplifier output signal 26 indicative of the patient's instantaneous inspiration volume. The amplifier output signal 26 is coupled to an analog-to-digital converter 30 for conversion into a digital signal 34 indicative of the patient's instantaneous inspiration volume which is coupled to the processor 14, as shown.

The patient interface 28 is provided in the form of a flexible conductor, or conductive loop, suitable for wrapping around and conforming to the patient's chest in an extensible manner (i.e., by expanding and contracting as the patient inhales and exhales, respectively). Various forms of the conductive loop 28 are suitable, such as a wire sewn into a flexible elastic belt which permits the wire to conform to the patient's body. Further suitable forms of the conductive loop 28 are shown and described in U.S. Pat. No. 4,815,473, 4,308,872, 4,807,640, 5,301,678 and 5,543,012, each of which is incorporated herein by reference. One suitable commercially available conductive loop is sold by Ambulatory Monitoring, Inc. of Ardsley, NY under the product name RESPIBAND.

In certain cases, it may be desirable to utilize a plurality of loops (i.e., illustrated by loops 28 and 28') adapted for being disposed around and conforming to different regions of the patient's chest or torso. In such applications, the loops are coupled in series in the amplifier circuit 24 of FIG. 3. The sum of the inductance of such series-coupled loops provides an indication of the change in the patient's inspiration volume.

The processor 14 stores the digital inspiration volume signal 34 in memory 16 and displays the measured inspiration volume on the display 18. To this end, the processor 14 is coupled to the display 18 via a digital Input/Output (I/O) card 21 which latches digital output signals from the processor 14 for coupling to the display 18. One suitable digital I/O card is of the type sold by Computerboards of Mansfield, Mass. More particularly. the measured inspiration volume is displayed on a first portion of the display 18. A target inspiration volume is generated by the processor 14 and displayed on a second portion of the display 18 in response to a predetermined function, such as a sine wave function. Preferably, the measured and target inspiration volume display portions are arranged to facilitate their comparison. In use, the patient, or subject, is instructed to breathe in a manner which causes the measured inspiration volume display portion to match the target inspiration volume display portion.

The processor 14 may take various forms, such as the microprocessor of a standard personal computer, workstation or other microprocessor-driven device. As one example, the processor 14 is an INTEL-compatible microprocessor of an IBM-compatible personal computer running the MICROSOFT WINDOWS graphical user interface. The memory 16 includes a Random Access Memory (RAM) and the user interface may include a keyboard, touch screen and/or mouse. In the illustrative embodiment, the user interface 20 includes a touch screen incorporated into the display 18, the display is a flat panel LCD display of the type sold by Goldstar and the processor 14 and memory 16 are typical components associated with an IBM-compatible personal computer. The analog-to-digital converter 30 is a commercially available component; such as is sold by Computerboards of Mansfield, MA under the part number DA51402116. It will be appreciated by those of ordinary skill in the art, that the apparatus and techniques of the system 10 may be implemented on various equipment, both hardware and software.

Figure 2:
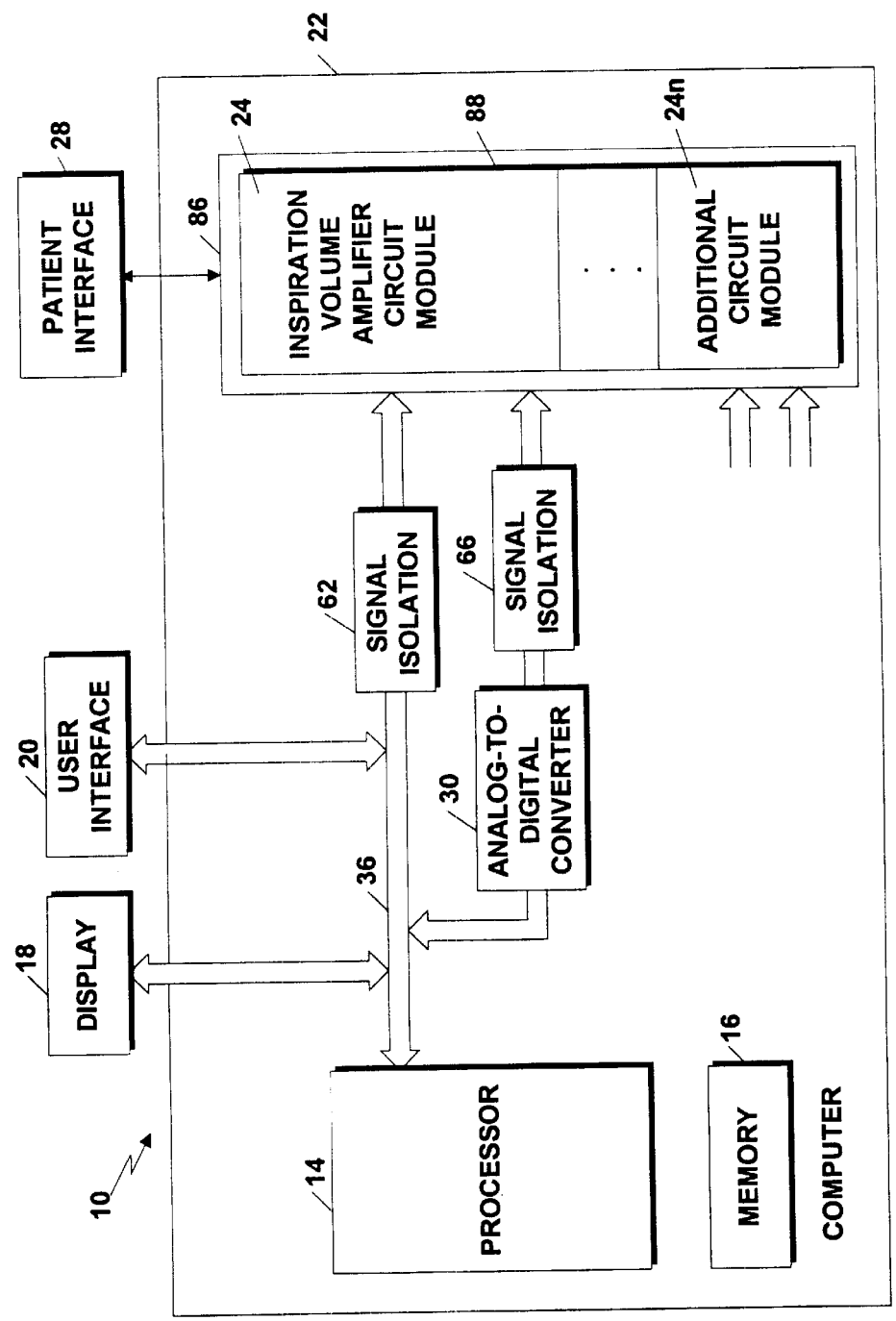
FIG. 2 is a block diagram of a computer-based implementation of the apparatus of FIG. 1.

Referring to FIG. 2, the inspiration volume amplifier 24 may be implemented in the form of a "circuit module" adapted for insertion into an Input/Output (O/I) port or slot 86 of a standard personal computer chassis 22. To this end, the circuit module 24 is housed in a metal or metallized-plastic box, or instrument chassis 88, which is adapted for insertion into an opening of the computer chassis 22 typically used for a diskette drive, tape drive or CD-ROM drive.

The system 10 may include additional circuitry (not shown) for measuring various other physiological signals of the patient, such as a blood pressure signal or an electrocardiogram signal, in which case such circuitry is implemented in the form of one or more additional circuit modules. The instrument chassis 88 has an open front face which permits insertion of one or more circuit module(s) therein. The front of any unused portions of the instrument chassis is covered by metal or metallized. panels. Advantageously, the instrument chassis serves as a "Gauss cage" to reduce electromagnetic interference (EMI).

With this arrangement. the processor 14 can communicate with and control the inspiration volume amplifier circuit module 24 via the computer's standard busses and the circuit module can draw on the power available to the computer components. The processor 14 transmits any control information to the circuit module 24 via the computer's digital control bus 36 and receives the digital version 34 of the analog amplifier output signal 26 via the computer's digital control bus 36. For safety reasons, it is preferable to isolate the computer bus 36 from the circuit module 24, for example, with the use of opto-isolators 62, 66, respectively.

Figure 3:
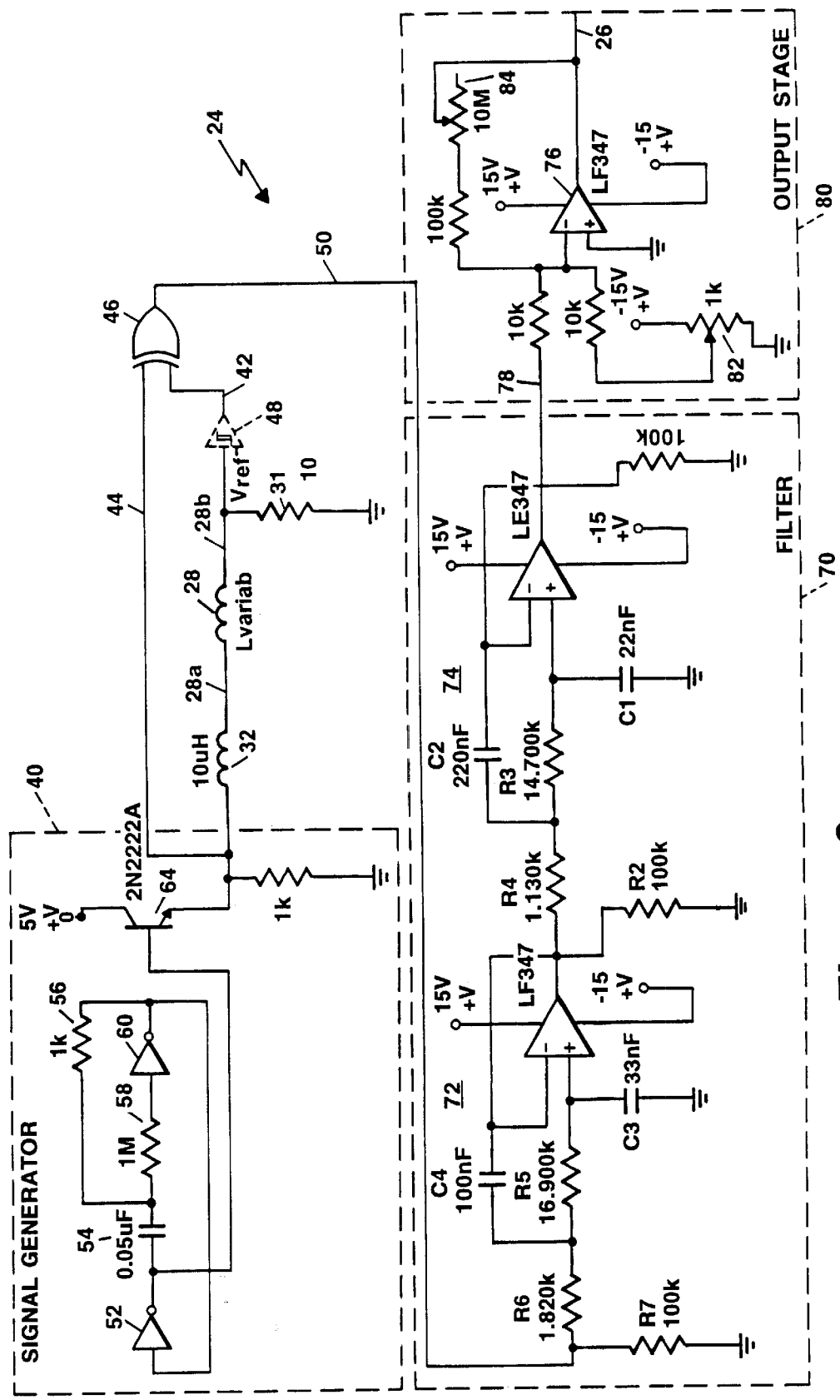
FIG. 3 is a schematic of the inspiration volume amplifier and patient interface of FIG. 1.

Referring to FIG. 3, the inspiration volume amplifier 24 is electrically connected to the conductive loop 28 (represented by the schematic symbol of an inductor). A signal generator 40 generates a square-wave signal 44 for coupling to first terminal 28a of the loop 28 via an inductor 32. A second terminal 28b of the loop 28 is coupled to a resistor 31, as shown.

Various circuitry is suitable for providing the signal generator 40. In the illustrative embodiment, the signal generator 40 is an oscillator circuit, including inverters 52, 60, a capacitor 54 and resistors 56, 58. The output of inverter 52 is coupled to the base of an npn transistor 64 having an emitter at which the square-wave signal 44 is provided. The transistor 64 provides current gain to the square-wave signal.

The inductance of inductor 32 and loop 28 has the effect of rounding the edges of the square-wave signal 44 to provide a pseudo-square-wave signal at the second terminal 28b of the inductor 28. Preferably, a comparator 48 is coupled to the second terminal 28b of the loop 28 as shown, in order to convert the pseudo-square-wave signal into a delayed square-wave signal 42. In the illustrative embodiment, the comparator 48 is provided with significant hysteresis, such as on the order of four volts, Use of the comparator 48 with hysteresis has the advantage of increasing noise immunity and providing an accurate and reliable threshold level Vref.

The amount of the delay between the square-wave signal 44 and the delayed square-wave signal 42 varies linearly with the variations in the inductance of loop 28. Stated differently, the signal at the second terminal 28b of the loop 28 is delayed as compared to the signal 44, with the amount of the delay being indicative of the inductance of loop 28 and thus, of the patient's instantaneous inspiration volume.

The inductor 32 is provided in order to increase the LC time constant between square-wave signal 44 and the pseudo-square-wave signal at loop terminal 28b. In the illustrative embodiment, inductor 32 is a $10_\mu H$ inductor and the conductive loop 28 has a nominal inductance of between approximately $3_\mu H$ and $5_\mu H$. In use, the inductance of the loop 28 varies on the order of between $0.02_\mu H$ and $0.004_\mu H$, depending on factors such as the size of the patient and the deepness of breathing. If the LC time constant is too small, then the delay between the square-wave signal 44 and the delayed square-wave signal 42 may be too small to measure accurately. Stated differently, the LC time constant needs to be at least as long as the time needed for the output of the comparator 48 and. the exclusive-OR gate 46 to respond.

It will be appreciated by those of ordinary skill in the art that the delay between. the square-wave signal 44 and the delayed square-wave signal 42 at the output of the comparator 48 can be measured using various circuitry and techniques. In the illustrative embodiment, an exclusive-OR gate 46 is provided for this purpose. A first input of the exclusive-OR gate 46 is responsive to the square-wave signal 44 and a second input is responsive to the delayed square-wave signal 42 at the output of the comparator 48.

Assuming that input signals 44 and 42 to the exclusive-OR gate 46 are initially at logic low levels, the output signal 50 of the exclusive-OR gate 46 transitions to a logic high level when the square-wave signal 44 goes high and transitions to a logic low level when the delayed square-wave signal 42 goes high. From the initial condition where both input signals 42, 44 to the exclusive-OR gate 46 are high, the output of the gate 46 goes high when the square-wave signal 44 goes low and goes low when the delayed square-wave signal 42 goes low. The output signal 50 thus has a duty cycle (i.e., ratio of the interval during which the signal is high to the total period) proportional to the delay between the signals 42 and 44 and thus, to the patient's inspiration volume.

Figure 3A:
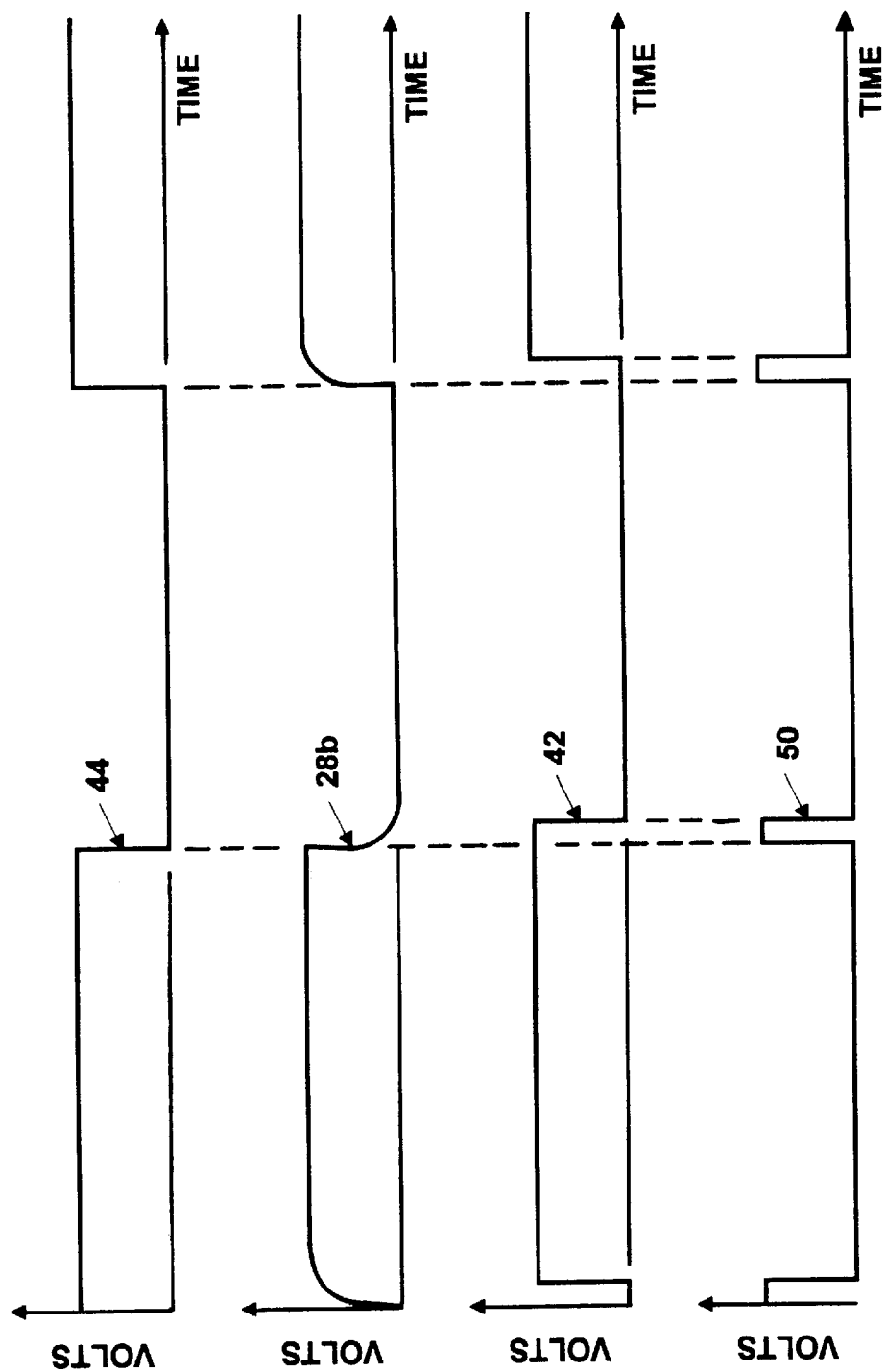
FIG. 3A shows various signal waveforms associated with the circuit of FIG. 3.

Referring also to FIG. 3A, the above-described operation of the exclusive-OR gate 46, as well as the relationship between various signals of circuit of FIG. 3 are illustrated. In particular, the signal waveforms shown in FIG. 3A include the square-wave signal 44, the pseudo-square-wave signal at terminal 28b, the output signal 42 of comparator 48 and the output signal 50 of the exclusive-OR gate 46, all drawn to the same time scale.

The output signal 50 of the exclusive-OR gate 46 is further processed by a filter 70 and an output stage. The filter 70 is a low pass filter which smoothes the output signal 50 in order to facilitate measurement of the delay between the square-wave signal 44 and the delayed square-wave signal 42. In particular, the low pass filter 70 provides a low-frequency signal 78 having an amplitude proportional to the duty cycle of the signal 50. In the illustrative embodiment, filter 70 is a fourth-order low pass filter comprising two stages 72 and 74 and having a nominal cutoff frequency of approximately 350 Hz. In general, the cutoff frequency should be selected to be high enough so that the filter output signal 78 adequately responds to changes in the inductance of loop 28 and low enough to substantially reduce ripple at the frequency of the signal generator 40.

The filter output signal 78 is coupled to an operational amplifier 76 of the output stage 80. The output stage 80 includes an offset adjustment control 82 in the form of a potentiometer coupled to the inverting input of the amplifier 76. The potentiometer 82 is user-adjustable in order to reduce or remove the DC offset of the signal 78. This can be achieved by displaying the filtered signal 78 on the display 18, thereby enabling the user to adjust the potentiometer 82 until the DC offset is reduced or removed. Alternatively, an automated method for removing the DC offset may be implemented.

The output stage 80 further includes a gain adjustment control 84 in the form of a potentiometer coupled in feedback relationship with the operational amplifier 76, as shown. Since the amplitude of the digital output signal 50 is attenuated by the filter 70, it is generally desirable to increase the gain by adjusting the potentiometer 84. Preferably, the gain is selected so that the voltage difference in the amplifier output signal 26 between full exhalation and full inhalation by the patient is on the order of two volts centered within the supply voltage range (e.g., zero to five volts). In the illustrative embodiment, the potentiometer 84 is adjustable to vary the gain by a factor of between 10 and 1000. The output signal 26 of the amplifier is an analog signal having an amplitude that varies linearly with changes in the patient's inspiration volume.

Figure 4:
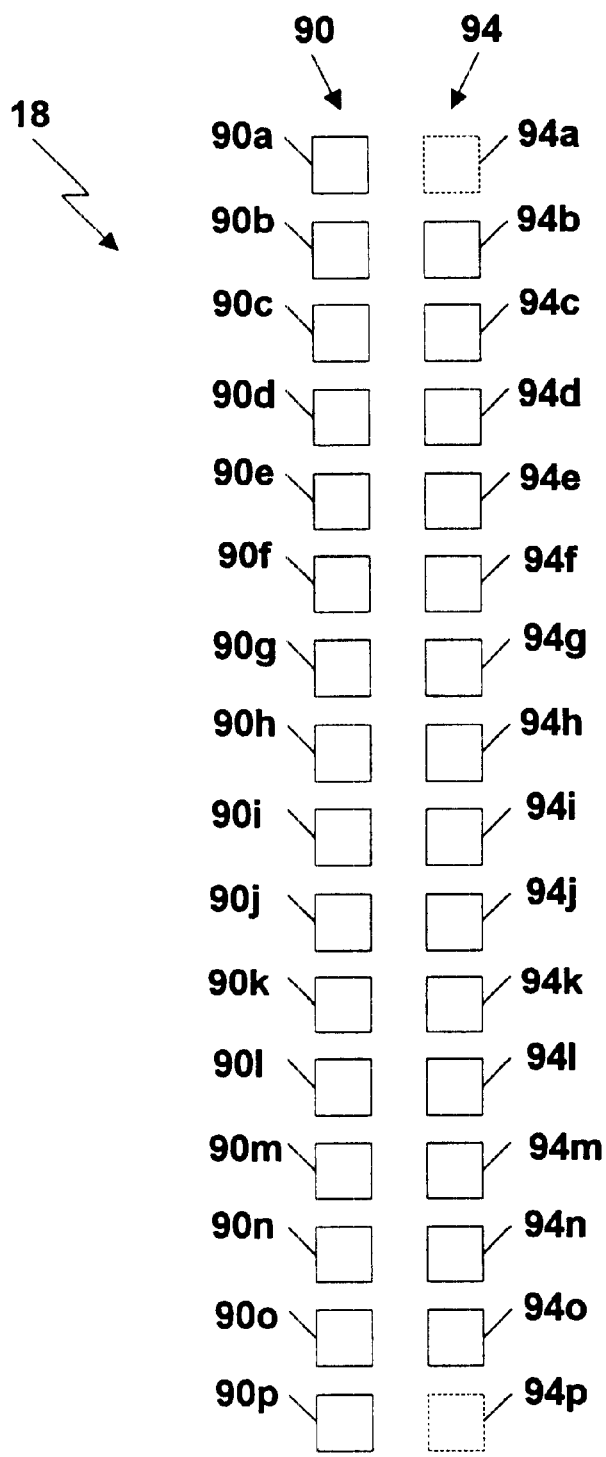
FIG. 4 illustrates the display of FIG. 1.

Referring to FIG. 4, the display 18 includes two portions 90 and 94. The first display portion 90 is used to display the patient's actual measured inspiration volume and the second display portion 94 is used to display a target, or desired inspiration volume to which the patient's breathing preferably conforms. In general, the target display portion 94 displays a predetermined breathing pattern including both an amplitude of inhalation and exhalation and a rate, or frequency. Preferably, the breathing pattern displayed on the target inspiration volume display follows a predetermined mathematical function, such as a sine wave function or a chirp function in which the frequency increases as a function of time. However, alternatively, the predetermined pattern may be a random pattern.

Each display portion 90, 94 includes a plurality of display elements 99a–9op, 94a–94p, respectively, and in the illustrative embodiment, includes sixteen light emitting diodes (LEDs). The LEDs of the display portions 90, 94 are arranged vertically in the form of bar graphs, as shown. Preferably, the display portions 90, 94 are disposed adjacent to one another in order to facilitate rapid visual comparison of the display elements, as will be described. It will be appreciated by those of ordinary skill in the art however, that various types of display elements and arrangements are possible and suitable in order to achieve the benefits described herein.

The bar graph display portions 90 and 94 are arranged such that illumination of each LED indicates a particular level, or range of lung volume. In the illustrative embodiment, the lowest LED corresponds to a greatest level of exhalation and the highest LED corresponds to a greatest level of inhalation. More particularly, with respect to the measured inspiration volume display portion 90, the lowest LED 90p indicates that the measured inspiration volume is less than a predetermined minimum level and the highest LED 99a indicates that the measured inspiration volume is greater than a predetermined maximum level.

The target display portion 94 is shown to include the same number of LEDs as the measured display portion 90, with each of the target LEDs 94a–94p disposed adjacent to, and preferably in substantial horizontal alignment with, a corresponding one of the LEDs 99a–90p of tile measured inspiration volume display portion 90. However, since the uppermost measured inspiration volume LED 99a and the lowermost measured inspiration volume LED 90p indicate that the patient's inspiration volume is either greater than or less than predetermined maximum and minimum levels, respectively, the corresponding LEDs 94a, 94p of the target display portion 94 are not utilized since these are not desired conditions. However, LEDs 94a and 94p may be included since the bar graph display portions 90, 94 may be used display other information.

In operation, one of tile LEDs in each of the display portions 90 and 94 is illuminated by the processor 14 at any given time. The illuminated one of the LEDs 94b–94o of the target display portion 94 indicates the desired level of inhalation or exhalation at the particular time; whereas, the illuminated one of the LEDs 99a–90p of the measured inspiration volume display portion 90 indicates the patient's present inspiration volume. The patient is instructed to breathe in a manner which causes the measured inspiration volume display portion 90 to illuminate the one of the LEDs 9db–90o which corresponds to, and preferably is horizontally aligned with, the illuminated one of the target LEDs 94b–94o. Stated differently, the patient is instructed to breathe so as to cause the measured display portion 90 to match, or follow the target display portion 94.

Figures 4A, 4B, 4C, 4D, 4E:
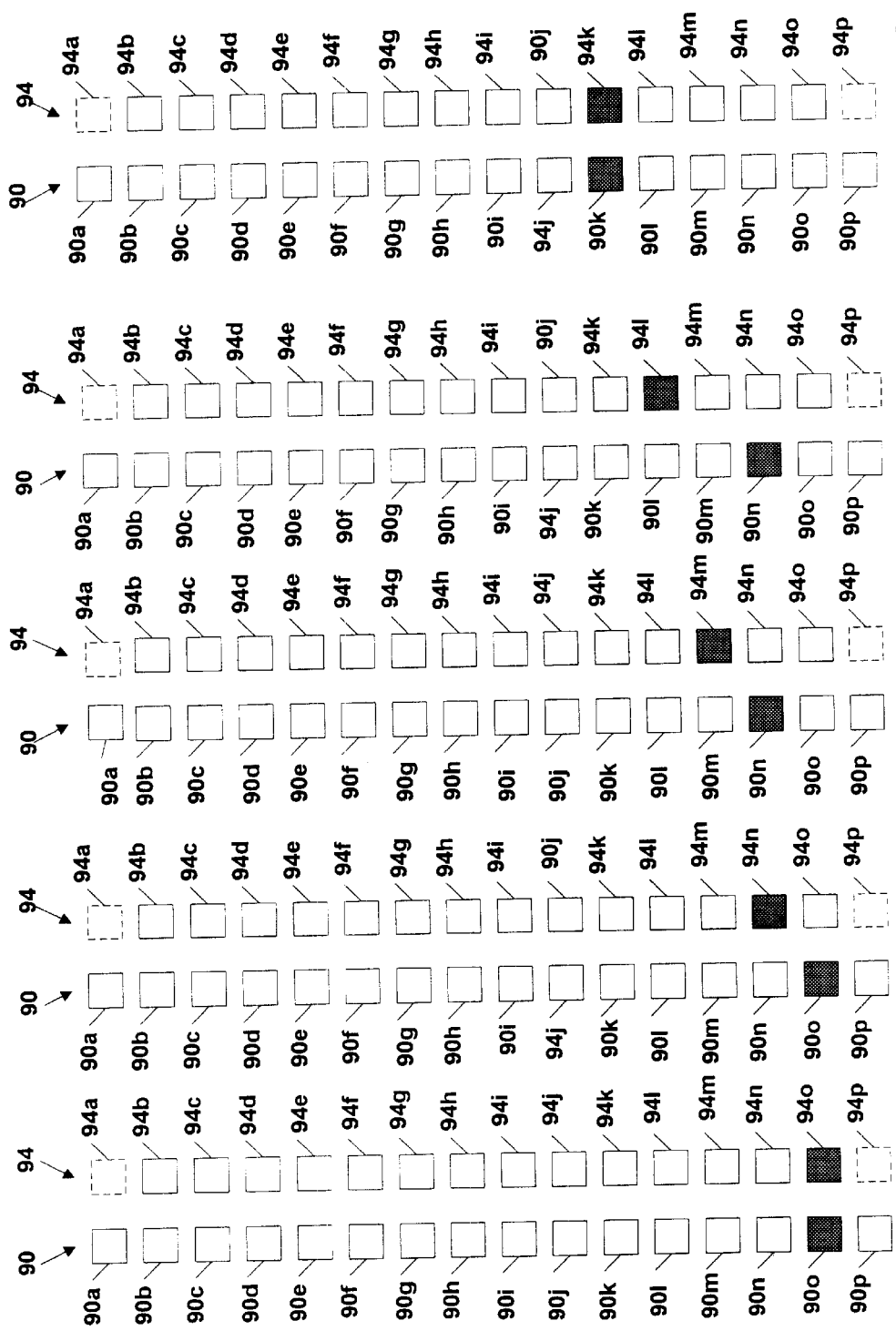
FIGS. 4A, 4B, 4C, 4D and 4E illustrate exemplary states of the display of FIG. 4 in operation.

FIGS. 4A–4E illustrate examples of various states of the display portions 90 and 94 during operation. The progression of FIGS. 4A–4E illustrates a target inspiration volume pattern in the form of a sine wave function shown on target display portion 94. In FIG. 4A, the target inspiration volume is indicated by illuminated LED 94o and the patient's actual inspiration volume matches the target volume since the horizontally aligned LED 90o is illuminated. In each of FIGS. 4B–4D, the discrepancy between the illuminated measured inspiration volume LED and the illuminated target inspiration volume LED indicates that the patient should increase his or her inspiration volume to comply with the target breathing pattern. In FIG. 4E, the patient's inspiration volume has caught up to, and matches the target inspiration volume since the measured inspiration volume LED 90k is illuminated when the horizontally aligned target inspiration volume LED 94k is illuminated.

Figure 5:
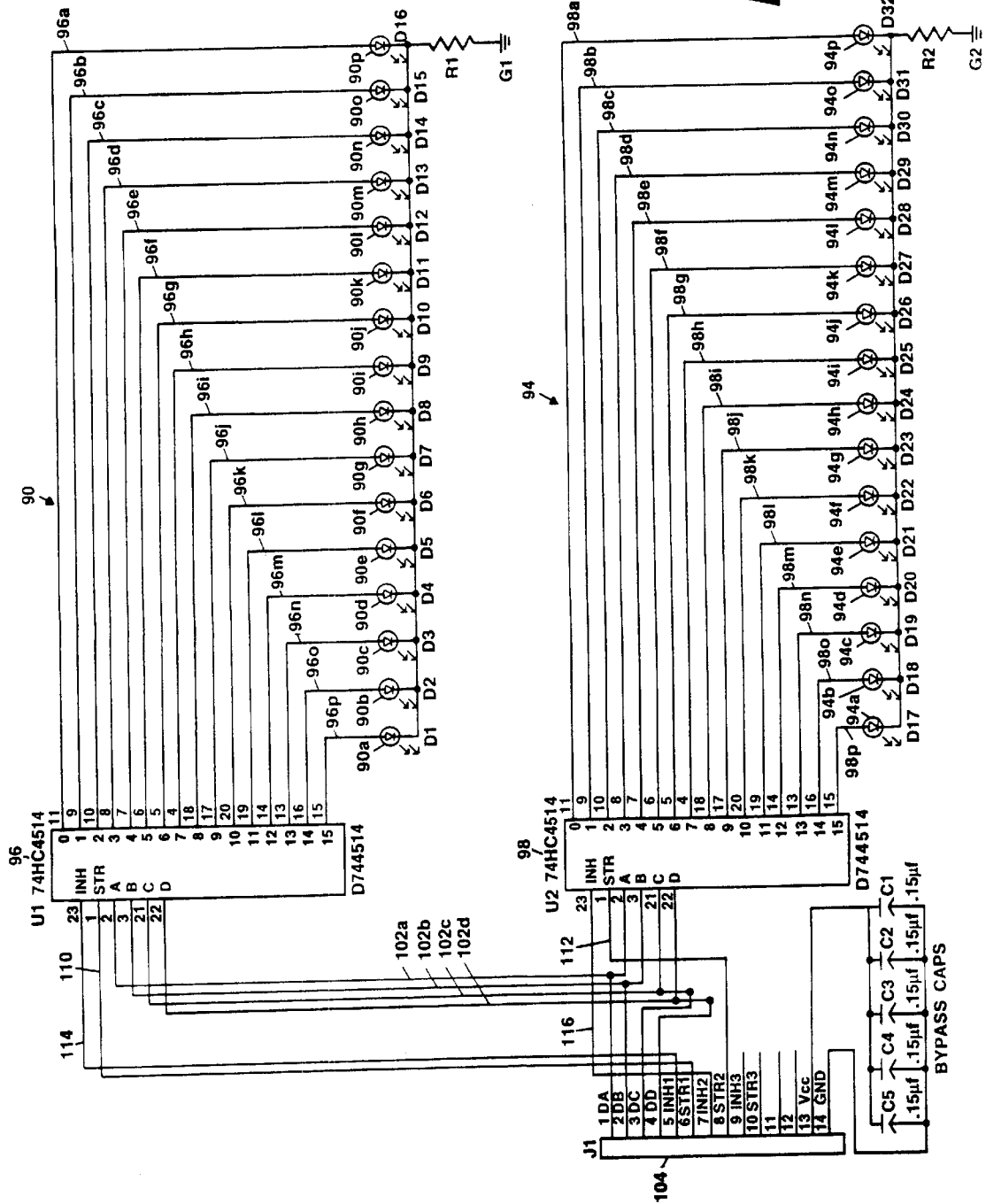
FIG. 5 is a schematic of the display of FIG. 4.

Referring to FIG. 5, each display portion 90, 94 includes a respective demultiplexer 96, 98 which is responsive to four data input signals 102a, 102b, 102c and 102d for providing digital output signals on signal lines 96a–96p, 98b–98o in order to illuminate an appropriate one of the LEDs 99a–90p, 94b–94o, respectively. In the illustrative embodiment, the demultiplexers 96, 98 are of the type sold by National Semiconductor of Santa Clara, Calif. under the product number 74HC4514. The processor 14 provides the four data input signals 102a–102d to each of the demultiplexers 96, 98 via the digital I/O board 21 (FIG. 1) which is coupled to a connector 104.

Each LED 99a–90p, 94a–94p is coupled between an output signal line of the respective demultiplexer 96, 98 and through a current limiting resistor to ground. More particularly, LEDs 99a–90p are coupled between output signal lines 96a–96p of demultiplexer 96 and LEDs 94a–94p are coupled between output signal lines 98a–98p of demultiplexer 98, respectively. Thus, when the demultiplexer output signal, on the respective signal line goes high, the corresponding LED is illuminated.

Also provided by the processor 14 to each of the demultiplexers 96, 98 via the digital I/O board 21 and connector 104 is a strobe signal 110, 112 and an inhibit signal 114, 116, respectively. The strobe signals 110, 112 control latching of the data input signals 102a–102d by the respective demultiplexer 96, 98. More particularly, a positive-going pulse on a strobe signal line causes the respective demultiplexer to capture, or latch in the data input signals and to provide output signals according to the following Table:

| Signal Line 102a | Signal Line 102b | Signal Line 102c | Signal Line 102d | Illuminated LED when strobe 110 high | Illuminated LED when strobe 112 high |
|---|---|---|---|---|---|
| 0 | 0 | 0 | 0 | 90p | |
| 0 | 0 | 0 | 1 | 90o | 94o |
| 0 | 0 | 1 | 0 | 90n | 94n |
| 0 | 0 | 1 | 1 | 90m | 94m |
| 0 | 1 | 0 | 0 | 90l | 94l |
| 0 | 1 | 0 | 1 | 90k | 94k |
| 0 | 1 | 1 | 0 | 90j | 94j |
| 0 | 1 | 1 | 1 | 90i | 94i |
| 1 | 0 | 0 | 0 | 90h | 94h |
| 1 | 0 | 0 | 1 | 90g | 94g |
| 1 | 0 | 1 | 0 | 90f | 94f |
| 1 | 0 | 1 | 1 | 90e | 94e |
| 1 | 1 | 0 | 0 | 90d | 94d |
| 1 | 1 | 0 | 1 | 90c | 94c |
| 1 | 1 | 1 | 0 | 90b | 94b |
| 1 | 1 | 1 | 1 | 90a | |

The inhibit signals 114,116 are active-high signals for the demultiplexers 96, 98. When an inhibit signal 114,116 is at disabling a logic the outputs of high level, all of the outputs of the respective demultiplexer are low, thereby turning off all of the 25 respective LEDs. During certain stages of operation, it may be desirable to turn off one or both of the display portions 90, 94, such as when other features of the system 10 and display 18 are in use.

Figure 6:
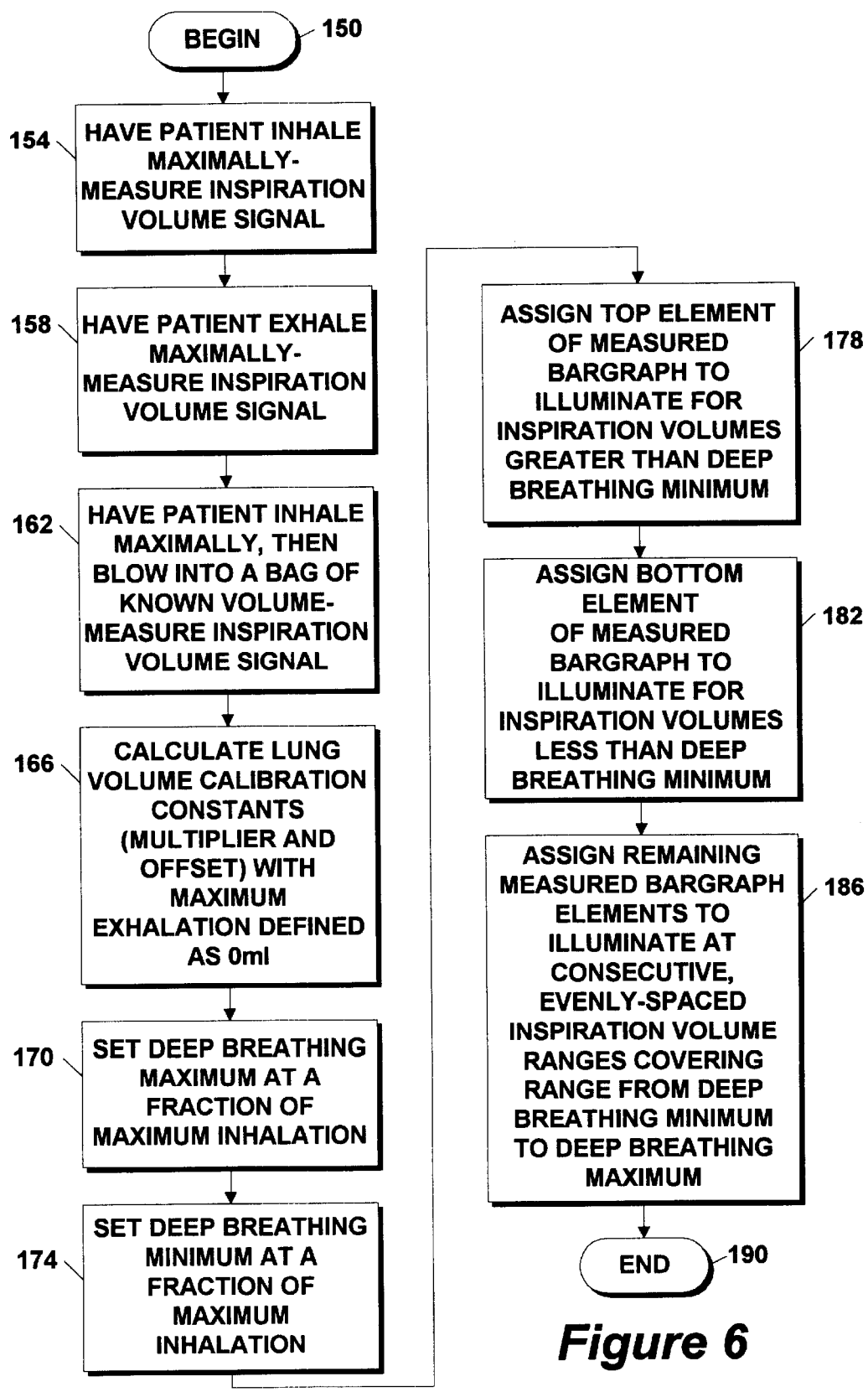
FIG. 6 is a flow diagram illustrating a method of calibrating the display of FIG. 4.

Referring to FIG. 6, a method of calibrating the display portions 90 and 94 commences in step 150, following which the patient, or subject is instructed to inhale as deeply as possible, to a maximal inhalation level in step 154. Also in step 154, the maximal inhalation level is measured by the inspiration volume amplifier 24 (FIG. 1) and the value of the output signal 34 is stored by the processor 14 in the memory 16. In subsequent step 158, the patient is instructed to exhale as deeply as possible, to a maximal exhalation level which is measured and stored in memory 16.

In step 162, the patient is instructed to inhale as deeply as possible and then to exhale into a bag of known volume, such as 800 mL, following which the inspiration volume amplifier 24 measures the patient's inspiration volume. This inspiration volume measurement thus provides a data point at which the measured inspiration volume is known to have a value equal to the maximal inhalation level minus the volume of the bag.

In step 166, the processor 14 calculates lung volume calibration constants for the patient, which include multiplier and offset constants used to convert the digital version 34 of the amplifier output signal 26 into a physical measure of the patient's inspiration volume, such as milliliters.

The calibration multiplier is determined in response to steps 154 and 162. The difference between the value of the digital version 34 of the amplifier signal 26 in steps 154 and 162 corresponds to the known volume of the bag. Thus, the number of milliliters represented by each voltage gradation is computed by setting the voltage difference between the inspiration volume signal measured in step 162 and the inspiration volume signal measured in step 154 equal to the volume of the bag, such as 800 mL.

In the illustrative embodiment, the maximum exhalation level is defined as zero milliliters. The offset constant is selected so that when it is added to the product of the voltage measured in step 158 and the calibration multiplier, it results in zero milliliters.

Having determined the subject's maximum inhalation volume and maximum exhalation volume, in process step 170, a predetermined fraction of the maximum inhalation volume is computed to define a deep breathing maximum. In the illustrative embodiment, the deep breathing maximum is approximately 85% of the patient's maximum inhalation volume. Similarly, in step 174, a predetermined fraction of the patient's maximum inhalation volume is computed and defines a deep breathing minimum. In the illustrative embodiment, the deep breathing minimum is 15% of the patient's maximum inhalation volume.

In step 178, the top LED 99a of the measured inspiration volume display portion 90 is assigned to illuminate whenever the measured inspiration volume exceeds the deep breathing maximum. Similarly, in step 182, the bottom LED 90p is assigned to illuminate whenever the measured inspiration volume is less than the deep breathing minimum.

Thereafter, in step 186, the range of inspiration volume represented by each of the remaining display elements 90b–90o and 94b–94o of the display portions 90, 94, respectively, is determined. To this end, the total volume between the deep breathing maximum and the deep breathing minimum is divided by the number display devices, following which the calibration process terminates in step 190. For example consider the case where the patient's deep breathing minimum is 150 mL and the deep breathing maximum is 850 mL. In this case, each of LEDs 90b–90o and 94b–94o represents approximately 50 mL of inspiration volume.

Figure 7:
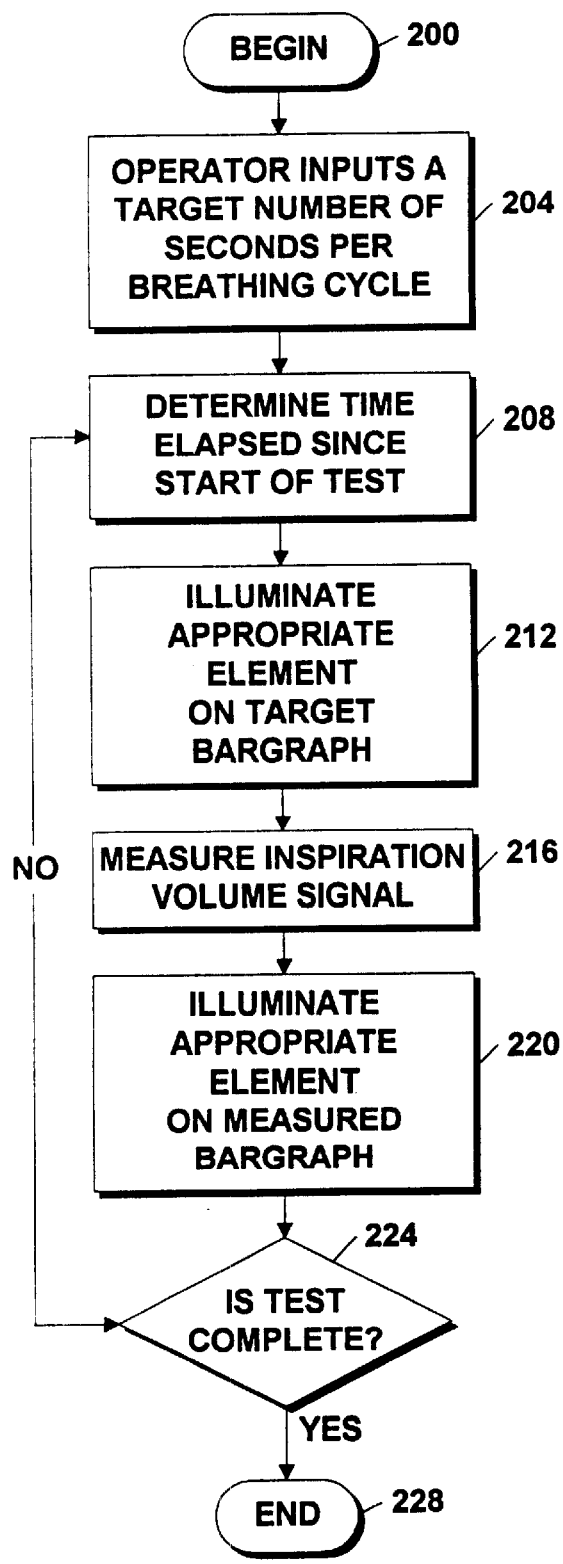
FIG. 7 is a flow diagram illustrating a method of operation of the system of FIG. 1.

Referring to FIG. 7, a method of operation of the processor 14 in driving the display portions 90 and 94 commences in step 200, following which the operator or user of the system enters a target breathing rate (i.e., a desired number of seconds per breathing cycle). As noted above, a typical target rate useful in neuropathy diagnosis is on the order of ten seconds per breathing cycle.

In step 208, the processor 14 determines how many seconds have lapsed since the beginning of the particular test. Thereafter, in step 212, the appropriate LED 94b–94o on the target display portion 94 is illuminated. In the illustrative embodiment, the target display portion 94 is controlled in accordance with a sine wave function and, specifically, according to the following equation:

$$(N-2-0.5)\sin\left(\frac{2\pi \cdot target\ breathing\ rate}{elapsed\ time}\right) + (N-2+0.5)$$

where N is the number of utilized LEDs 94b–94o of the target display portion. The integer portion of the result of the above equation indicates the number of the LED that is activated (i.e., where {LED 94o is LED one, LED 94n is LED two, etc.). The processor 14 activates the appropriate LED by providing the data input signals 102a–102d at the appropriate logic levels according to the Table above and the lung volume range assigned to each LED 94b–94o in calibration steps 186 (FIG. 6) and by providing a positive-going pulse on the strobe signal line 112 to the demultiplexer 98 (FIG. 5).

Once the appropriate LED on the target inspiration volume display portion 94 is illuminated, the actual inspiration volume is measured by sampling the amplifier output signal 34 (FIG. 1) in step 216. Thereafter, in step 220, the processor 14 activates the appropriate LED on the measured display portion 90 in accordance with the value of the digital signal 34, the lung volume range assigned to each LED 99a–90p in calibration steps 178, 182 and 186 (FIG. 6) and the Table provided above.

In subsequent step 224, it is determined whether the test is complete. Typically, the patient's inspiration volume is measured over a predetermined interval measured by a timer associated with the processor 14. If the test is not yet complete, then the process is repeated starting at step 208. Alternatively, the process is terminated in step 228. Use of lung volume as a feedback parameter in order to get a patient to breathe in a predetermined manner provides an improvement over the conventional use of audio tones to prompt a patient's breathing. However, in systems in which the inspiration volume is measured by measuring inspiration flow and converting the flow signal into a volume signal, inaccuracies occur. In particular, in computing the integral of the measured flow signal, an error would occur in the resulting volume signal whereby the volume signal would not return to its starting point at the end of any given breath cycle and this error is compounded over multiple breath cycles.

Certain physiological tests require that a patient breathe to a percentage of his or her maximum lung capacity at a predetermined frequency and for a predetermined duration. One such test is the metronomic deep breathing test used in heart rate variability analysis. While providing a patient with feedback as to measured lung volume as described above in connection with FIGS. 1–7 is one way of achieving a desired inspiration volume, it has been found that the use of inspiration flow for this purpose has advantages. In particular, a target inspiration flow pattern is easier for a patient to emulate than a target lung volume pattern. As a result, the extent to which the measured inspiration flow matches the target inspiration flow is increased and the repeatability of the inspiration tests is enhanced. Further, when inspiration flow is measured and then integrated to provide the feedback inspiration volume signal, an error can accumulate over time by which the inspiration volume signal does not return to its starting amplitude at the end of each breathing cycle. Use of measured inspiration flow for providing patient feedback does not suffer from this problem.

Figure 8:
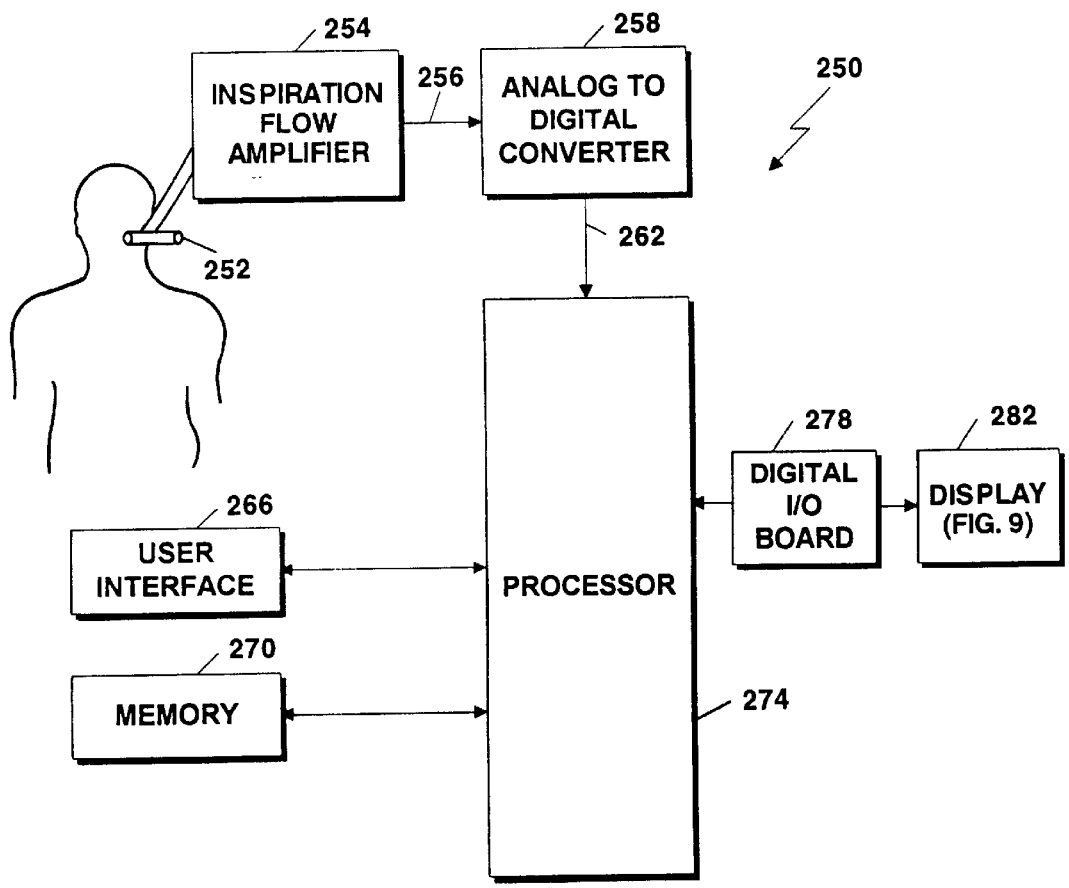
FIG. 8 is a block diagram of a medical diagnostic system including apparatus for measuring inspiration flow and for enhancing patient compliance with a predetermined breathing pattern.

Referring to FIG. 8, a system 250 for enhancing patient compliance with a predetermined breathing pattern utilizes patient feedback based on inspiration flow. The system 250 includes a patient interface 252 for measuring the patient's inspiration flow. Various devices 252 are suitable for this purpose. One suitable is available from Fukuda Sangyo Co. Ltd. of Japan and includes a mouthpiece having two chambers divided by a restriction. Both of the chambers are coupled through tubes to a pressure transducer in the amplifier 254 for measurement of the differential pressure between the chambers. It will be appreciated by those of ordinary skill in the art that various conventional flow measuring devices may be used to provide the patient interface 252.

The remaining components of the system 250 are substantially identical to like components of the system 10 described above in conjunction with FIG. 1, except for the differences as noted below. The inspiration flow amplifier 254 amplifies the pressure transducer output signal to provide an amplified signal 256 to an analog-to-digital converter 258. The analog-to-digital converter 258 converts the amplified output signal 256 into a digital signal 262 indicative of the patient's instantaneous inspiration flow for coupling to a processor 274.

The processor 274 displays the measured inspiration flow on a display 282. To this end, The processor 274 is coupled to the display 282 through a digital input/output (O/I) card 278 which latches digital output signals from the processor 274 for coupling to the display 282.

The processor 274 further controls the display 282 to display a target inspiration flow. The processor 274 is otherwise substantially identical to the processor 14 of FIG. 1 and thus may take the various forms and be provided by the same commercially available components as described above in connection with processor 14. Further, the memory 270 and the user interface 266 are substantially identical to memory 16 and user interface 20 of FIG. 1 and thus may take the various forms described above. The components comprising the system 250 may be arranged in the form of circuit modules adapted for insertion into a standard personal computer chassis as described above in connection of FIG. 2.

Figure 9:
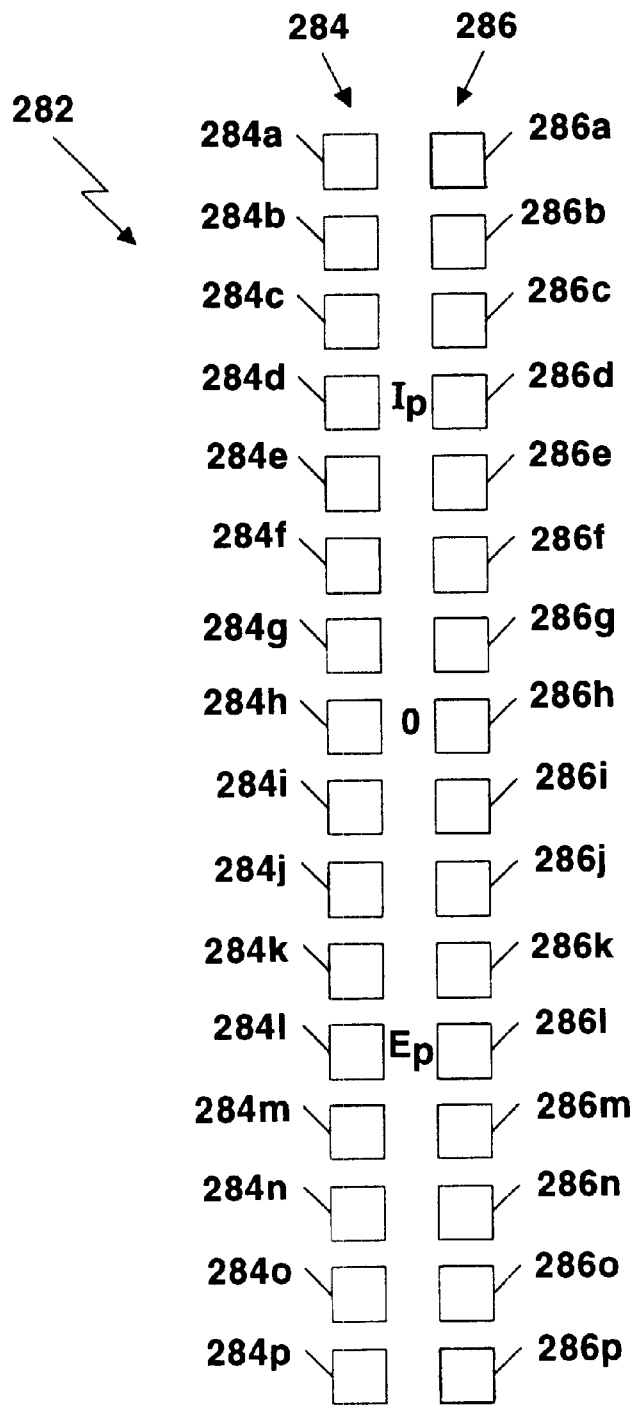
FIG. 9 illustrates the display of FIG. 8.

Referring also to FIG. 9, the display 282 includes a first display portion 284 for displaying the measured inspiration flow signal and a second display portion 286 for displaying a target inspiration flow signal. Each display portion 284, 286 includes a plurality of display elements 284a–284p, 286a–286p, respectively. In the illustrative embodiment, each such display portion includes sixteen LEDs, but the number of LEDs can be readily varied. In some applications, it may be desirable to use more LEDs, such as on the order of between 16 and 64 LEDs, in order to enhance the resolution of the display.

The LEDs of each display portion 284, 286 are arranged vertically in the form of a bar graph, as shown. Preferably, the display portions 284, 286 are disposed adjacent to one another in order to facilitate rapid visual comparison of the display elements. It will be appreciated by those of ordinary skill in the art, however, that various types of display elements and arrangements are possible in order to achieve the benefits of the present invention. For example, in some applications it may be desirable to use an odd number of display elements in order to provide a centered LED as a "zero" reference point.

The display portions 284, 286 are arranged such that illumination of each LED indicates a particular level, or range of inspiration flow (i.e., rate of breathing). The uppermost LED corresponds to the greatest rate of inhalation and the lowermost LED corresponds to the greatest rate of exhalation.

According to a further aspect of the invention, the measured display portion 284 includes a maximum inhalation flow display portion including LEDs 284a–284c and a minimum exhalation flow display portion including LEDs 284m-284p. The maximum inhalation flow indicator LED 284c is illuminated when the patient's inhalation flow exceeds a predetermined maximum level Ip by a first predetermined amount, the maximum inhalation flow indicator LED 284b is illuminated when the patient's inhalation flow exceeds the predetermined maximum level Ip by a second, greater predetermined amount, and the maximum inhalation flow indicator LFD 284a is illuminated when the patient's inhalation flow exceeds the predetermined maximum level Ip by a third, greatest predetermined amount. Similarly, the minimum exhalation flow indicator LEDs 284m-284p are illuminated when the patient's exhalation flow falls below a predetermined minimum level Ep by a corresponding predetermined amount, with LED 284p indicating the greatest deviation between the patient's inspiration flow and the predetermined minimum level Ep.

With this arrangement, the efficacy of the system 250 in having a patient's breathing conform to the target breathing pattern is enhanced. This is because the patient is provided with the additional information that his or her breathing rate is either greater than or less than predetermined maximum and minimum levels and to what extent, respectively. The target inspiration flow display portion 286 may include the same number of LEDs as the measured inspiration flow display portion 284 or, alternatively, may omit the uppermost and lowermost LEDs 286a–286c and 286m–286p in horizontal alignment with measured inspiration flow LEDs 284a–284c and 284m–284p. This is because the uppermost and lowermost measured inspiration flow elements 284a–284c and 284m–284p are used to indicate that the patient's inspiration flow is either greater than or less than is ever desired. Thus, even when target LEDs 286a–286c and 286m–286p are present, they are not used.

In operation, one of the LEDs in each of the display portions 284, 286 is illuminated by the processor 274 at any given time. The illuminated one of the EDs 286d–286l of the target display portion 286 indicates the desired level or range of inspiration flow between a target inhalation rate Ip and a target exhalation rate Ep, with the LED 286h representing a zero reference point, or mean resting state. The illuminated one of the LEDs 284a–284p of the measured inspiration flow display portion 284 indicates the patient's present inspiration flow. The patient is instructed to breathe in a manner which causes the measured inspiration flow display portion 284 to illuminate the one of the LEDs 284d–284l which corresponds to (such as by horizontal alignment) with the illuminated one of the targets LEDs 286d–286l. That is, the patient is instructed to breathe so as to cause the measured display portion 284 to match, or follow the target display portion 286.

It will be appreciated by those of ordinary skill in the art that, alternatively, more than one of the LEDs in each of the display portions 284, 286 may be illuminated by the processor 274 at any given time. In particular several adjacent LEDs in each of the display portions 284, 286 may be illuminated. With such an arrangement, the display portions 284, 286 display the measured and target inspiration flows in bar graph patterns.

In the illustrative embodiment, the range of inspiration flow from greatest rate of inhalation to greatest rate of exhalation is distributed equally among each LED of the display portions 284, 286. However, it will be appreciated by those of ordinary skill in the art that other distributions may be implemented. As one example, the LED resolution may be greater near the predetermined maximum level Ip and the predetermined minimum level Ep (i.e., difference between inspiration flow levels represented by adjacent LEDs near the Ip and Ep levels is smaller than in other regions of the displays).

The circuitry which controls and actuates the LEDs of the display 282 is substantially identical to like circuitry which controls and actuates the LEDs of display 18 (FIG. 4). It will be appreciated by those of ordinary skill in the art, however, that various modifications and alternatives to the display circuitry of FIG. 4 are possible while still achieving the benefits of the subject invention.

Figure 10:
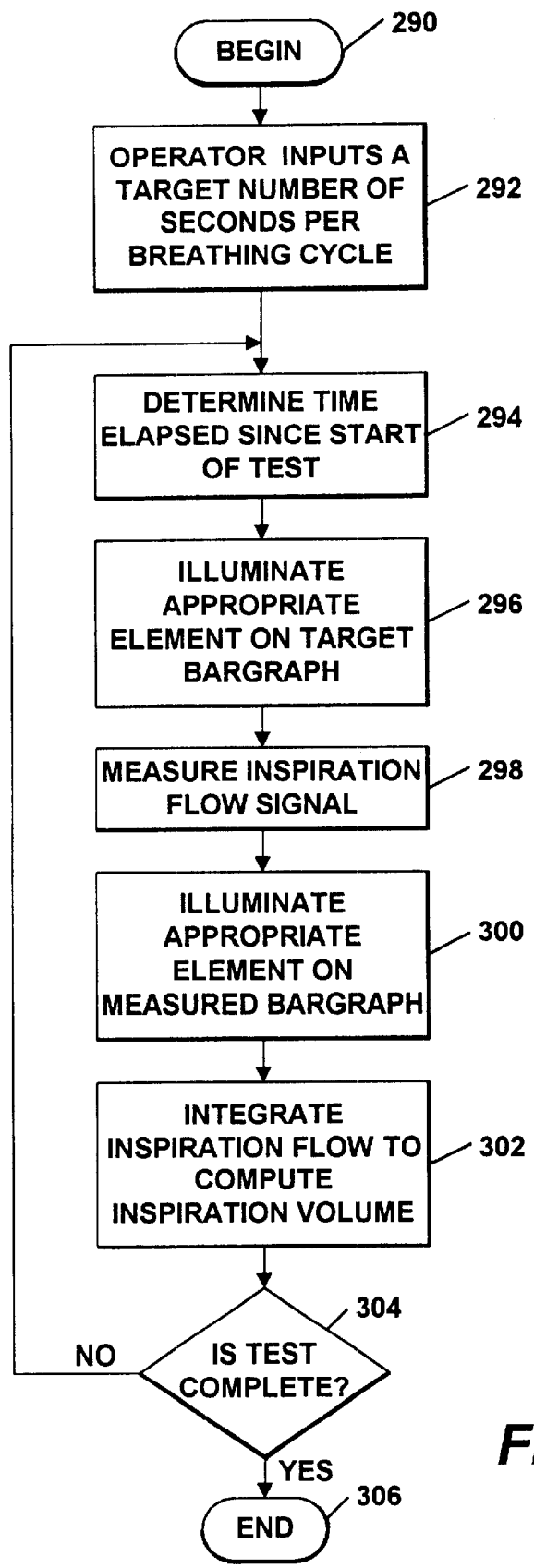
FIG. 10 is a flow diagram illustrating a method of operation of the medical diagnostic system of FIG. 8.

Referring also to FIG. 10, a flow diagram illustrates operation of the processor 274 in implementing the above-described inspiration flow feedback system 250. The process begins in step 290, following which an operator inputs a target number of seconds per breathing cycle in step 292, for example through user interface 266 (FIG. 8). As one example, in performing the metronomic deep breathing test, the operator inputs ten in order to prompt the patient to breathe at a rate of 0.1 Hz. In step 294, the time which has lapsed since the start of the test is determined. With this information, the processor 274 computes where in a particular target inspiration flow pattern the patient's inspiration flow should be in order to determine which target inspiration LED 286d–286l to illuminate.

In step 296, the appropriate element on the target display 286 is illuminated. In particular, the processor 274 illuminates the appropriate LED by providing data input signals at the appropriate logic levels, such as with the use of the above table and according to an inspiration flow range assigned to each LED 286d–286l as described below in conjunction with the calibration flow diagram of FIG. 12.

The actual inspiration breath flow is measured by sampling the amplifier output signal 256 (FIG. 8) in step 298. Thereafter, in step 300, the processor 274 activates the appropriate LED of the measured display portion 284 in accordance with the value of the digital signal 262 and the inspiration flow range assigned to each LED 284a–284p during the calibration process described below. As discussed, the patient is instructed to breathe so as to cause the measured inspiration flow which is fed back to the patient on display portion 284 to match the target inspiration flow. Process steps 292–300 are repeated for the duration of the inspiration measurement.

It will be appreciated by those of ordinary skill in the art that the sequence of displaying the target inspiration flow and the measured inspiration flow can be readily varied. More particularly, steps 296 and 300 are independently controlled and synchronized by the processor 274. Steps 296 and 300 may or may not occur substantially simultaneously. However, steps 296 and 300 are synchronized so that the displayed target flow and measured flow correspond to the same time after the testing has commenced. Further, while the patient's inspiration flow is generally measured at a relatively high rate, such as on the order of 500 samples/second, updating the measured inspiration flow display portion 284 at this rate would be counterproductive since a patient could not modulate his or her breathing fast enough to follow such a rapidly changing display. Thus, the measured inspiration flow signal may be buffered by the processor 274 and be displayed at a much slower rate, such as on the order of 30 samples/second.

The metronomic deep breathing test used in heart rate variability assessment systems requires a patient to inhale to a percentage of the patient's lung capacity, such as 80%, for a predetermined duration, such as 5 seconds and then to exhale to the patient's mean resting state, for the predetermined duration at a predetermined frequency, such as on the order of 6 breaths/minute, or 0.1 Hz. The accuracy and repeatability of the metronomic deep breathing test benefit significantly from the described inspiration flow feedback.

In accordance with a feature of the invention, in process step 302, the measured inspiration flow signal is integrated to compute the inspiration volume signal. The inspiration volume is used to calibrate the display 282 when performing the metronomic deep breathing test as will be described in conjunction with FIG. 12.

The measured inspiration flow data may be validated by determining whether or not the patient followed the prescribed breathing pattern to within a predetermined tolerance. In the illustrative metronomic deep breathing test, the computed volume is processed for this purpose as follows. Six peaks of the measured volume signal are averaged and the result is compared to 80% of the patient's maximum lung capacity to ensure that the patient was inhaling to the necessary extent. Also, the breath frequency may be computed to determine whether or not the rate of breathing was within a predetermined tolerance of the target 0.1 Hz. One illustrative way to determine the sufficiency of the breath rate is to average the frequency of several breath cycles and compare the result to the desired 0.1 Hz. As one example, if the patient's volume signal over six breaths is within +/−15% of the target 80% and the breath frequency is within +/−5% of the desired 0.1 Hz, then the measured inspiration flow data is determined to be valid.

In subsequent step 304, it is determined whether the test is complete. Typically, the patient's inspiration flow is monitored over a predetermined interval measured by a timer associated with the processor 274 according to the particular test being performed. If the test is not yet complete, then the process is repeated starting at step 294. Alternatively, the process is terminated in step 306.

Figure 11:
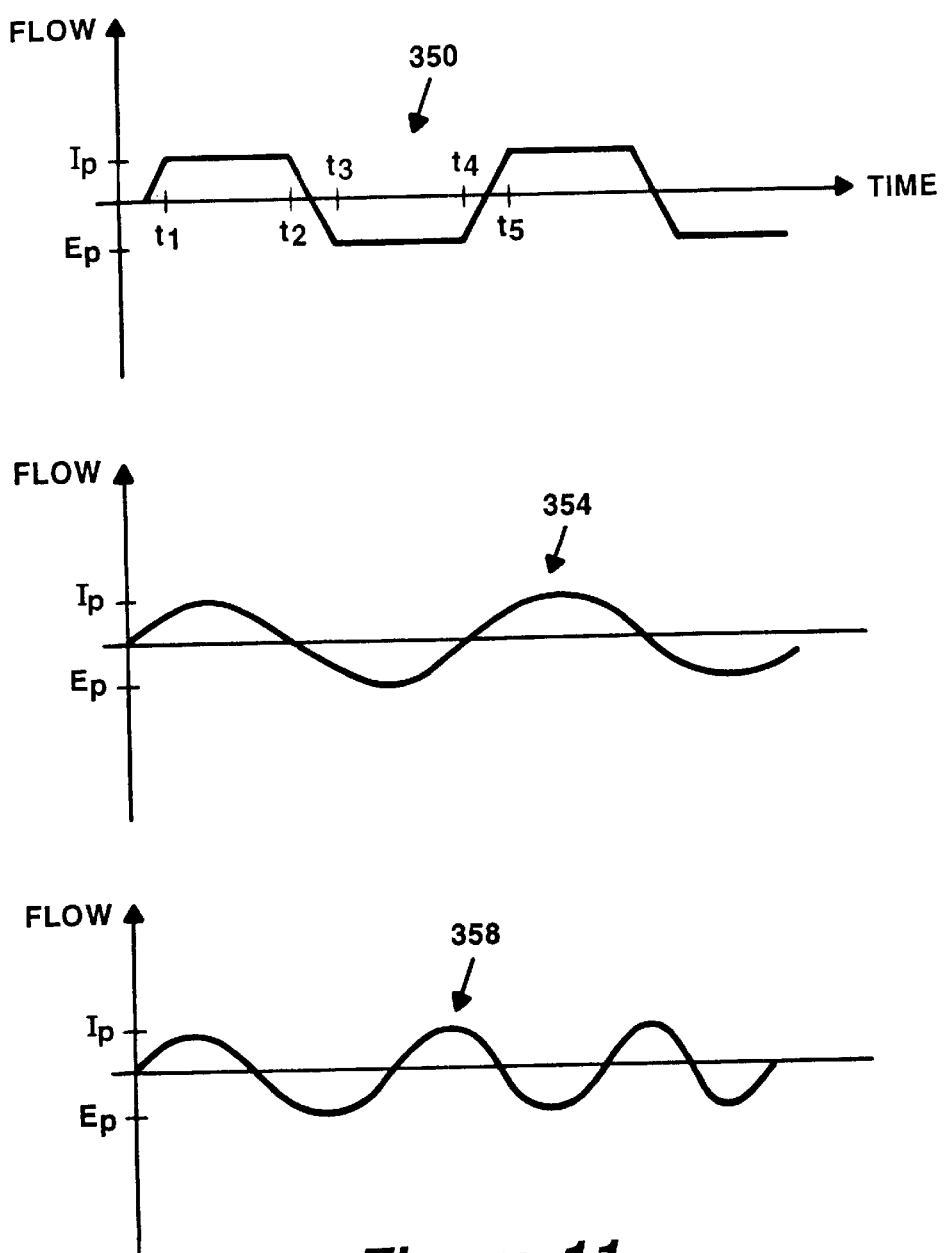
FIG. 11 shows several illustrative target inspiration flow waveforms.

Referring also to FIG. 11, three illustrative command signals for controlling the target inspiration flow display portion 286 are shown. As noted above, preferably, the target inspiration flow follows a predetermined pattern, such as a mathematical pattern. Illustrative command signal 350 is a trapezoidal signal according to which the patient is instructed to inhale to a predetermined target inhalation rate Ip and then to exhale at a predetermined exhalation rate Ep. According to this target inspiration flow command signal, the uppermost target LED 286d is illuminated from time $t_1$–$t_2$ and the lowermost target LED 286l is illuminated from time $t_3$–$t_4$. Between times $t_2$ and $t_3$, the target LEDs 286e–286k are sequentially illuminated and between times $t_4$ and $t_5$, the target LEDs 286k–286e are sequentially illuminated.

In the metronomic deep breathing test, the ideal target inspiration flow pattern is a square wave signal. However, since it is felt that it would be difficult for a patient to follow a display that toggles substantially instantaneously from uppermost LED being illuminated to lowermost LED being illuminated, a trapezoidal or triangular waveform for the target display may be preferred. If such a trapezoidal or triangular waveform is used, the target inhalation flow level Ip and exhalation flow Ep are increased and decreased, respectively, in order to compensate for the loss of inspiration flow during the transition times from the uppermost to the lowermost target display LED (e.g., from time $t_2$ to $t_3$ and time $t_4$ to $t_5$).

An alternative command signal 354 for the target display portion 286 follows a sine wave function. A further alternative command signal 358 is provided in the form of a chirp function in which the frequency of the signal increases with time, as shown. Still further, the command signal for the target display portion may be a combination of two or more predetermined functions, such as a sine wave function, a square wave function, a trapezoidal function, or a chirp function.

Figure 12:
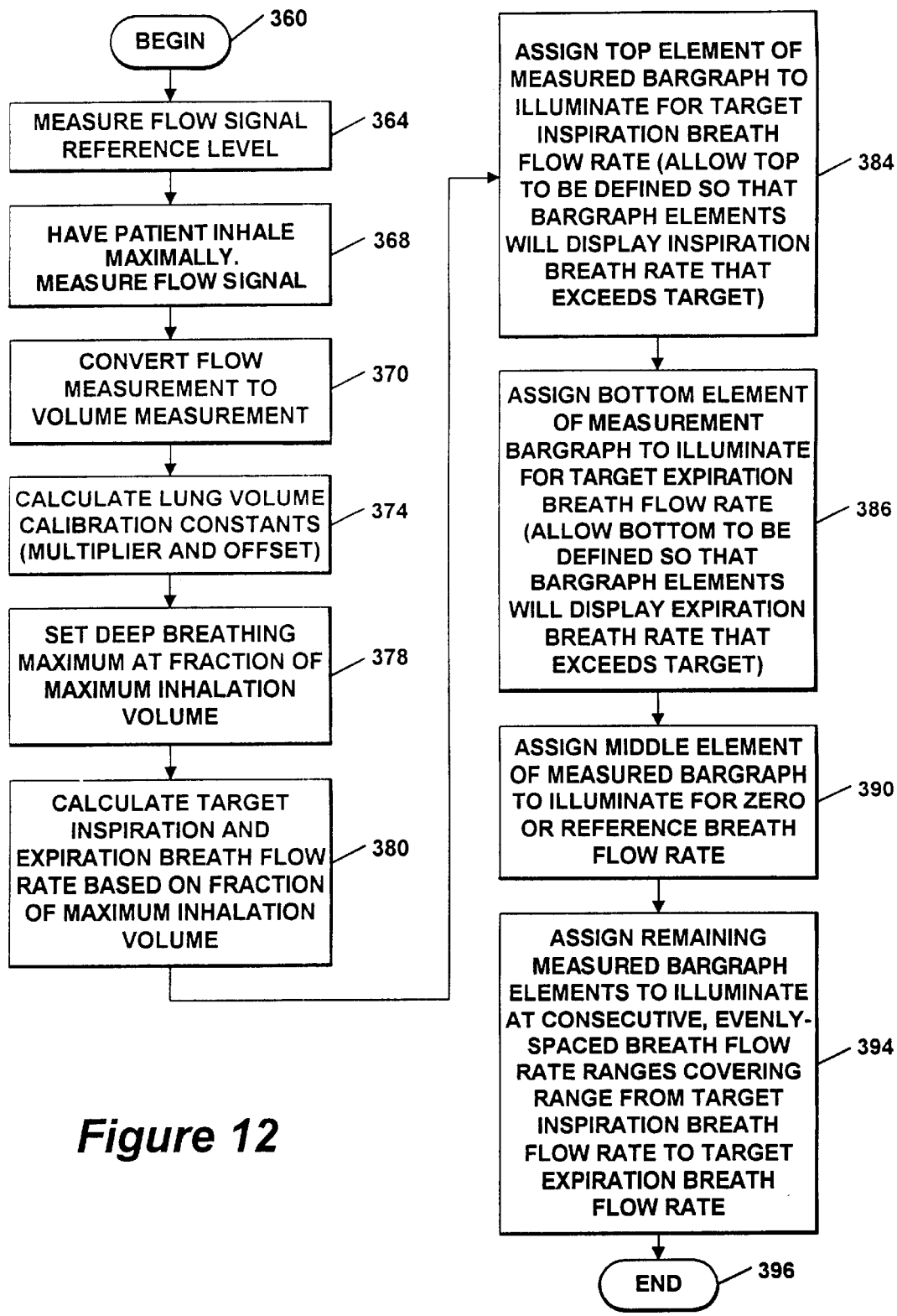
FIG. 12 is a flow diagram illustrating a method of calibrating the display of FIG. 8.

Referring to FIG. 12, a method for calibrating the display 282 of FIG. 8 is illustrated. The process begins in step 360 following which an inspiration flow reference level is measured in step 364. The reference level is simply the measured inspiration flow signal when the patient is not breathing into the patient interface 252. This becomes the "zero" breath flow rate and its value is stored by the processor 274 in memory 270.

In step 368, the patient is instructed to inhale as deeply as he or she is capable and the resulting flow signal is measured by the inspiration flow amplifier 254. Subsequently, in step 370, the measured inspiration flow signal is converted to an inspiration volume signal. This is achieved by integrating the measured inspiration flow signal over the duration that the flow signal was measured. The resulting inspiration volume signal represents a maximum lung volume capacity and is then stored in memory 270 by processor 274.

In step 374, the maximum lung capacity is used to calculate calibration constants which include a multiplier and an offset constant used to convert the digital version 262 of the amplifier output signal 256 into a relative measure of the patient's inspiration volume. More particularly, the offset constant is provided by the flow signal reference level measured in step 364 and the multiplier is a value calculated to permit the measured inspiration flow to be converted into the inspiration flow scale represented by the measured flow display portion 284.

In step 378, the maximum lung volume is used to calculate a deep breathing maximum for use when performing metronomic deep breathing tests and the deep breathing maximum is stored in memory 270. In particular, the deep breathing maximum is approximately 80–85% of the patient's maximum lung volume.

In step 380, the deep breathing maximum volume is used to calculate a target inhalation rate Ip (FIG. 11) and a target exhalation rate Ep (FIG. 11). In the illustrative metronomic deep breathing example, given a deep breathing maximum volume 3 liters, and a desired breath frequency of 0.1 Hz, the resulting target inspiration flow Ip would be to 2.4 liters/5 seconds and the target exhalation rate Ep would be -2.4 liters/5seconds.

In step 384, the top LED 284a of the measured inspiration flow display portion 284 is assigned to illuminate whenever the measured inspiration flow exceeds the target inhalation flow Ip by a predetermined amount. In step 386, the LED 284p is assigned to illuminate whenever the measured inspiration flow is less than the target exhalation flow Ep by a predetermined amount. These predetermined amounts are a function of the total number of target elements used to span the Ip to Ep range and the total number of measured display LEDs and are selected so that the measured display elements 284d, 284l represent the target inhalation rate Ip and target exhalation rate Ep, respectively. In step 390, a zero, or reference LED 284h is assigned to illuminate whenever the measured inspiration flow matches the reference or zero breath flow. In step 394, the range of inspiration flow represented by illumination of each of the remaining display elements 284b–284o and 286b–286o is determined. In particular, the total flow rate between the maximum inhalation flow represented by LED 284a and the maximum exhalation flow represented by LED 284p is divided by the number of display devices, following which calibration terminates in process step 396.

Having described the preferred embodiments of the invention, it will now become apparent to one of ordinary skill in the art that other embodiments incorporating their concepts may be used. It is felt therefore that these embodiments should not be limited to disclosed embodiments but rather should be limited only by the spirit and scope of the appended claims. All publications and references cited herein are expressly incorporated herein by reference in their entirety.

What is claimed is:

1. A system for improving patient compliance with a predetermined breathing pattern during inspiration measurements comprising:
    (a) a device for measuring the inspiration flow of a patient;
    (b) a display comprising:
        a first display portion for displaying the measured inspiration flow of the patient;
        a second display portion disposed adjacent to the first display portion for displaying a target inspiration flow: and
    (c) a processor responsive to the measured inspiration flow of the patient for controlling the first display portion, wherein the processor is operative to control the second display portion in accordance with a predetermined mathematical function.

2. The system of claim 1 wherein said first display portion is for displaying only the instantaneous measured inspiration flow of the patient and the second display portion is for displaying only an instantaneous target inspiration flow.

3. The system of claim 1 wherein said predetermined mathematical function is selected from a sine wave function, a square wave function, a trapezoidal function, a chirp function, or a combination of two or more of a sine wave function, a square wave function, a trapezoidal function, and a chirp function.

4. A system for improving patient compliance with a predetermined breathing pattern during inspiration measurements, comprising:
   (a) a device for measuring the inspiration flow of a patient for heart rate variability analysis;
   (b) a display comprising:
      a first display portion for displaying the measured inspiration flow of the patient; and
      a second display portion disposed adjacent to the first display portion for displaying a target inspiration flow; and
   (c) a processor responsive to the measured inspiration flow of the patient for controlling the first display portion, wherein the processor is operative to control the second display portion in accordance with a predetermined function.

5. The system of claim 4 wherein said processor is further responsive to the measured inspiration flow for computing the inspiration volume of the patient and for processing said inspiration volume to compute a deep breathing maximum level for use in a metronomic deep breathing test.

6. A method for improving patient compliance with a predetermined breathing pattern during inspiration measurements comprising of:
   measuring the inspiration flow of a patent;
   displaying the measured inspiration flow of the patient;
   displaying a target inspiration flow, said target inspiration flow following a predetermined mathematical function; and
   instructing the patient to breathe so as to cause the measured inspiration flow to match the target inspiration flow.

7. The method of claim 6 wherein said measured inspiration flow displaying step comprises displaying only the instantaneous measured inspiration flow of the patient and said target inspiration flow displaying step comprises displaying only an instantaneous target inspiration flow.

8. The method of claim 6 wherein said predetermined mathematical function is selected from a sine wave function, a square wave function, a triangular function, a trapezoidal function, a chirp function or a combination of two or more of a sine wave function, a square wave function, a trapezoidal function, and a chirp function.

9. A method for improving patient compliance with a predetermined breathing pattern during inspiration measurements, comprising the steps of:
   measuring the inspiration flow of a patient;
   displaying the measured inspiration flow of the patient;
   displaying a target inspiration flow;
   instructing the patient to breathe so as to cause the measured inspiration flow to match the target inspiration flow;
   computing the inspiration volume of the patient in response to the measured inspiration flow; and
   computing a deep breathing maximum level for use in performing a metronomic deep breathing test.

10. A system for improving patient compliance with a predetermined breathing pattern comprising:
    (a) a device for measuring the inspiration flow of a patient;
    (b) a display for displaying the measured inspiration flow of the patient, wherein said display comprises:
       (i) a maximum flow display portion for indicating when the patient's inhalation flow exceeds a predetermined maximum level, wherein said predetermined maximum level is a function of said measured inspiration flow of the patient; and
       (ii) a minimum flow display portion for indicating when the patient's exhalation flow falls below a predetermined minimum level, wherein said predetermined minimum level is a function of said measured inspiration flow of the patient; and
    (c) a processor for controlling said display in accordance with said measured inspiration flow of the patient.

11. The system of claim 10 wherein said display further comprises a target inspiration flow portion for displaying a target inspiration flow.

12. The system of claim 11 wherein said processor controls said target inspiration flow portion according to a predetermined mathematical function.

13. A method for improving patient compliance with a predetermined breathing pattern during inspiration measurements, comprising the steps of:
    measuring a patient's inspiration flow;
    computing a maximum inhalation flow level as a function of the patient's measured inspiration flow and a minimum exhalation flow level as a function of the patient's measured inspiration flow;
    displaying the measured inspiration flow of the patient on a measured inspiration flow display, including when said measured inspiration flow is greater than said maximum inhalation flow level and when said measured inspiration flow is less than said minimum exhalation level;
    displaying a target inspiration flow on a target inspiration flow display in accordance with a predetermined function; and
    instructing the patient to breathe in a manner that causes the measured inspiration flow display to match the target inspiration flow display.

14. The method of claim 13 wherein said predetermined function is selected from a sine wave function, a square wave function, a triangular function, a trapezoidal function, a chirp function or a combination of two or more of a sine wave function, a square wave function, a trapezoidal function, and a chirp function.

* * * * *

UNITED STATES PATENT AND TRADEMARK OFFICE
CERTIFICATE OF CORRECTION

PATENT NO. : 6,436,053 B1
DATED : August 20, 2002
INVENTOR(S) : Keith N. Knapp, II et al.

It is certified that error appears in the above-identified patent and that said Letters Patent is hereby corrected as shown below:

Column 5,
Line 17, reads "metallized." and should read -- metallized --.

Column 6,
Line 12, reads "and." and should read -- and --.
Line 14, reads "between." and should read -- between --.
Line 39, reads "of circuit" and should read -- of the circuit --.

Column 7,
Line 34, reads "99a" and should read -- 90a --.
Line 34, reads "9op" and should read -- 90p --.
Lines 55, 61 and 63, reads "99a" and should read -- 90a --.

Column 8,
Line 10, reads "99a" and should read -- 90a --.
Line 15, reads "9db" and should read -- 90b --.
Lines 42, 50 and 53, reads "99a" and should read -- 90a --.

Column 9,
Line 24, reads "at disabling a logic the outputs of" and should read -- at a logic --.

Column 10,
Lines 12 and 65, reads "99a" and should read -- 90a --.
Line 22, reads "number display" and should read -- number of display --.
Line 37, reads ".14" and should read -- 14 --.

Column 12,
Line 25, reads "arc" and should read -- are --.

Column 13,
Line 12, reads "EDs" and should read -- LEDs --.

UNITED STATES PATENT AND TRADEMARK OFFICE
CERTIFICATE OF CORRECTION

PATENT NO.   : 6,436,053 B1
DATED        : August 20, 2002
INVENTOR(S)  : Keith N. Knapp, II et al.

It is certified that error appears in the above-identified patent and that said Letters Patent is hereby corrected as shown below:

<u>Column 17,</u>
Line 34, reads "patent" and should read -- patient --.

Signed and Sealed this

Fifth Day of August, 2003

JAMES E. ROGAN
*Director of the United States Patent and Trademark Office*